(12) United States Patent
Chen

(10) Patent No.: US 11,534,628 B2
(45) Date of Patent: Dec. 27, 2022

(54) METHOD OF RADIATION POSITION

(71) Applicant: National Central University, Taoyuan (TW)

(72) Inventor: Ei-Fong Chen, Taoyuan (TW)

(73) Assignee: NATIONAL CENTRAL UNIVERSITY, Taoyuan (TW)

( * ) Notice: Subject to any disclaimer, the term of this patent is extended or adjusted under 35 U.S.C. 154(b) by 0 days.

(21) Appl. No.: 17/511,584

(22) Filed: Oct. 27, 2021

(65) Prior Publication Data

US 2022/0134134 A1 May 5, 2022

(30) Foreign Application Priority Data

Oct. 30, 2020 (TW) ................................ 109137925

(51) Int. Cl.
*A61N 5/10* (2006.01)
(52) U.S. Cl.
CPC ........ *A61N 5/1075* (2013.01); *A61N 5/1049* (2013.01); *A61N 2005/105* (2013.01); *A61N 2005/1087* (2013.01)
(58) Field of Classification Search
None
See application file for complete search history.

(56) References Cited

U.S. PATENT DOCUMENTS

| | | | | |
|---|---|---|---|---|
| 7,594,752 B2* | 9/2009 | Rockseisen | .......... | A61N 5/1049 378/205 |
| 2004/0022363 A1* | 2/2004 | Ghelmansarai | ........ | A61B 6/583 378/206 |
| 2015/0352376 A1* | 12/2015 | Wiggers | ................... | A61B 6/06 378/207 |
| 2020/0315567 A1* | 10/2020 | Constantin | .......... | A61N 5/1075 |

* cited by examiner

*Primary Examiner* — Hoon K Song
(74) *Attorney, Agent, or Firm* — Hannah Tien

(57) ABSTRACT

The present invention is a method of radiation position, which includes: placing a locking bar member on a proper position of a treatment bed; selecting positions respectively on two sides of the treatment bed to be joined with two ends of the locking bar member; and providing a calibration device, wherein the calibration device is provided with at least one positioning point, so that the bottom part of the calibration device is buckled with at least two positioning elements on the locking bar member; and calculating an offset distance between an irradiation point of a radiation and the at least one positioning point of the calibration device to obtain a value, wherein if the value is less than a deviation value, it represents completion of a positioning. The purpose of the present invention is to provide a method of quick and precise radiation position, which can not only reduce time cost but also increase the daily use frequency of a radiological apparatus to facilitate cost recovery.

10 Claims, 4 Drawing Sheets

METHOD OF RADIATION POSITION

FIELD OF THE INVENTION

The present invention relates to a method of radiation position, especially a method of less time cost, less labor cost, and a simpler and more precise method than prior arts.

BACKGROUND OF THE INVENTION

Regardless of the kind of radiation therapy is used, traditionally, before each patient is treated, the basic process of daily quality assurance (Daily QA) of currently available radiological apparatuses is carried out. The purpose is to ensure smooth subsequent processes and to avoid unnecessary damages to other normal tissues or cells of the patient caused by high-energy radiation.

The present invention mainly focuses on the part of calibration of the Daily QA items. In the past, lights were turned off to create an environment in a dark condition, and the calibration process was carried out by using at least two laser beams, a positioning line on a detector and human naked eyes. However, minor deviations caused by three factors, including the width of the laser beams (about 3 to 5 mm), the width of the positioning line, and the human naked eyes, must be considered. In addition, the laser beam is subjected to a problem of annual deviation of 1 to 2 mm. The operation is too complicated if Lynx+Sphinx adopted by IBA in 2015 is used as a daily quality assurance device. More than 20 minutes per day are spent on the daily quality assurance. The current process of radiation calibration is time consuming. It takes from 1 to 5 minutes to complete the process.

Besides, the current radiation position norms are primarily based on photon therapy, and very few additional regulations regarding proton therapy discussed recently have been made. Compared to photon therapy, proton therapy has completely different characteristics, which makes it more focused on the importance of positioning, for example, after photon rays are irradiated, the phenomenon of diffusion usually ensues. On the contrary, the phenomenon of scattering as proton beam interacts with material is relatively small, and after the Bragg peak is achieved upon reaching the tumor tissue, no more dose remains. The effect of suppressing or treating the patient's tumor can only be achieved by giving a higher dose of radiation. The requirements of precision of positioning is even more rigorous than those of the photon rays.

Therefore, the purpose of the present invention is to propose a method of rapid radiation position, which can not only reduce the time cost but increase the daily use frequency of a radiological apparatus to facilitate cost recovery. In addition, the human-eye laser positioning is replaced with mechanical precision, allowing the radiation to target the lesion more accurately, thereby reducing the chance of damaging other normal tissues or cells.

DETAILED DESCRIPTION OF THE INVENTION

Regarding the quality assurance specifications of radiotherapy machines, three major parts including radiation safety, machinery, and dose are inspected individually. Among the daily quality assurance items, one of them is localizing laser, which is primarily classified under the category of machine, the purpose is to determine the irradiation location of the radiation, which is then adjusted in coordination with the position of the patient to achieve the important step of precision treatment.

According to the recommendation of the current International Commission on Radiation Unit and Measurements (ICRU), the total dose uncertainty given to a patient must be less than 5%, in addition to the dose, the adjustment of the patient's posture, and the accuracy of the radiation beam, each step must be strictly controlled, and the quality assurance operation is even more important.

The present invention is a method of radiation position, which includes: placing a locking bar member on a proper position of a treatment bed; selecting positions respectively on two sides of the treatment bed to be joined with two ends of the locking bar member; and providing a calibration device, wherein the calibration device is provided with at least one positioning point, so that the bottom part of the calibration device is buckled with at least two positioning elements on the locking bar member; and calculating a horizontal/vertical offset distance between an irradiation point of a radiation and the at least one positioning point of the calibration device to obtain a value, wherein if the value is less than a deviation value, it represents completion of a positioning.

In one embodiment, a method of radiation position of the present invention, wherein the radiation is X-ray, photon ray, carbon ion, proton ray or other particle rays.

In another embodiment, a method of radiation positon of the present invention, wherein the radiation is proton ray.

In one embodiment, a method of radiation position of the present invention, wherein any one end of the locking bar member is provided with a fixing member, and the fixing members are joined with one side of the treatment bed to ensure that the locking bar member is not prone to loose.

In another embodiment, a method of radiation position of the present invention, wherein two ends of the locking bar member are respectively provided with fixing members, and the fixing members are joined with two sides of the treatment bed to ensure the locking bar member is not prone to loose.

In one embodiment, a method of radiation position of the present invention, wherein the fixing members are joined with the treatment bed in a manner of screw fastening, buckling, or clamping.

In another embodiment, a method of radiation position of the present invention further includes a tank body for accommodating the calibration device, wherein the bottom part of the tank body is provided with at least two holes, and the holes can be joined with the positioning elements of the locking bar member.

In one embodiment, a method of radiation position of the present invention, wherein the positioning elements of the locking bar member are round, square, triangular or in any other shapes.

In a preferred embodiment, a method of radiation position of the present invention, wherein the positioning elements are respectively designed in different shapes as desired, so as to prevent the direction of the calibration device from being in an opposite condition.

In one embodiment, a method of radiation position of the present invention, wherein the deviation value is 2 mm.

In one preferred embodiment, a method of radiation position of the present invention, wherein the deviation value is 1 mm.

In one more preferred embodiment, a method of radiation position of the present invention, wherein the deviation value is 0.5 mm.

The "deviation value" described in the instant specification is the value of the offset distance from the positioning point each time when a positioning is done with radiation and is used to determine whether the radiation is aligned with the positioning point on a detector/sensor when the radiation is irradiated. If the deviation value exceeds a specific value, it is considered that the treatment bed or the radiological apparatus is required to be further readjusted. Therefore, it is the allowable value required for laser positioning in accordance with the quality assurance regulations for radiotherapy machines.

EXAMPLES

Figure 1:
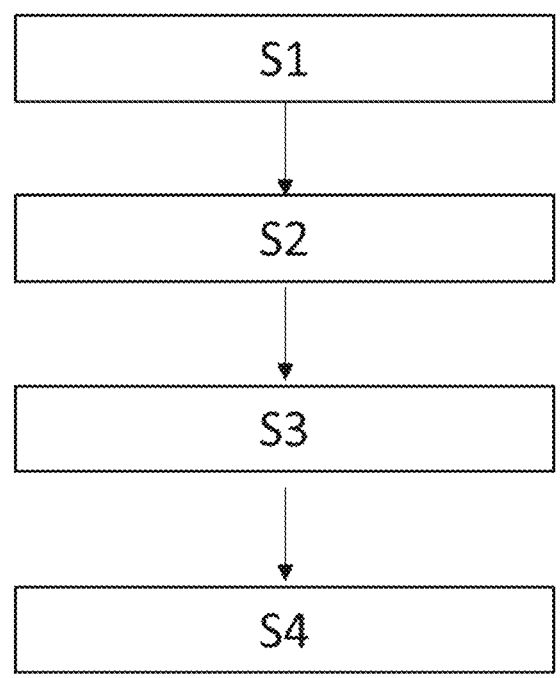
FIG. 1 is a flowchart of the method according to one embodiment of the present invention.

In order to enable examiners to have further knowledge and understanding of the features, purposes and functions of the present invention, the methods and functions of the present invention are described below so that the examiners can understand the features of the present invention. The detailed description is provided as follows:

As shown in FIG. 1, the present invention was a method of radiation position, which included: placing a locking bar member on a proper position of a treatment bed 2 (step S1); selecting a position on one side of the treatment bed 2 to be joined with one end of the locking bar member 1 (step S2); providing a calibration device 3, wherein the calibration device 3 was provided with at least one positioning point, so that the bottom part of the calibration device 3 was buckled with at least two positioning elements on the locking bar member 1 (step S3); and calculating an offset distance between an irradiation point of a radiation and the at least one positioning point of the calibration device 3 to obtain a value (step S4), wherein if the value was less than a deviation value, it represented completion of a positioning.

When no radiological apparatus was used, the treatment bed 2 was raised to a position close to an isocenter 5, when the radiation position process was to be performed, the treatment bed 2 was vertically lowered to a specific height. The purpose was to provide a space for accommodating the calibration device 3. When implementing the present invention, the "specific height" refers to the total height sufficient to accommodate the locking bar member plus the tank body itself or the ½ center of the total height of the tank body itself.

Step S1 was to place a locking bar member 1 on a proper position of a treatment bed 2. The locking bar member 1 used in the present invention was composed of carbon fibers. The proper position mentioned in the instant specification was that when the radiological apparatus was calibrated for the first time, the center of the radiation must pass through the isocenter 5, and it was used as a factor for determining whether or not the radiation position was successfully completed, as a result, the locking bar member was placed in a position in the vicinity of the isocenter 5 of the radiological apparatus.

Figure 2:
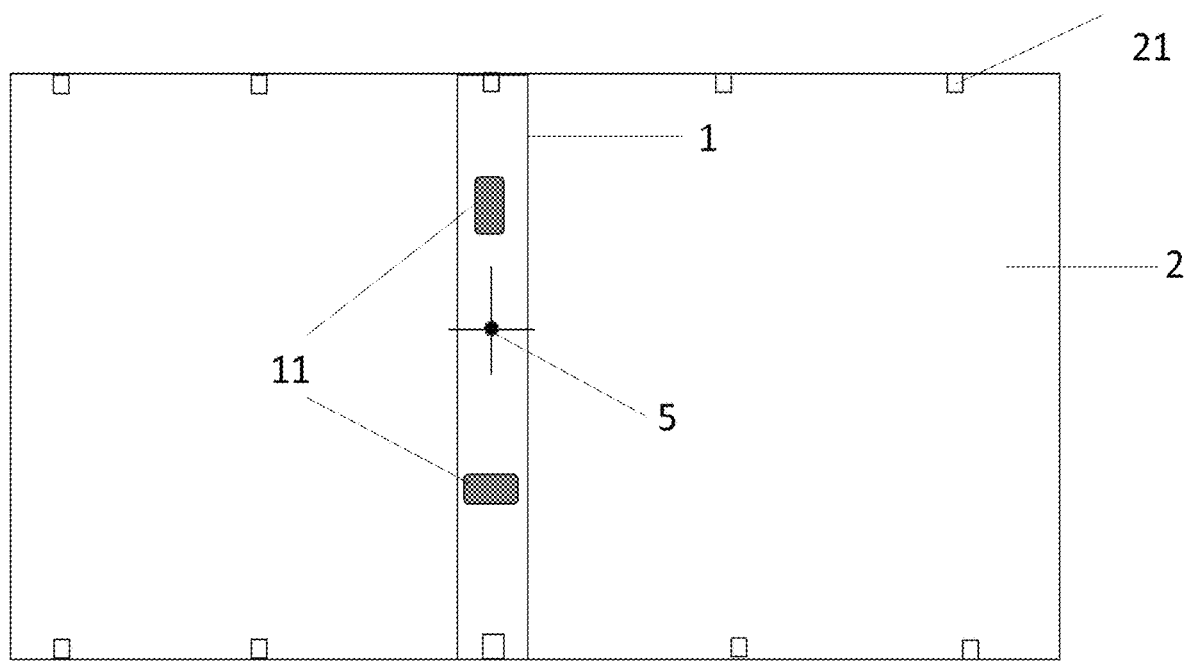
FIG. 2 is the top view of one embodiment of the present invention.

Next was step S2, on one side of the treatment bed 2, a position was selected to be joined with one end of the locking bar member 1. As shown in FIG. 2, in addition to be fixedly joined through one side, it was also possible to select two sides as a method of fixation. A plurality of holes 21 were provided at relative positions on both sides of the current treatment bed 2. After proper positions were confirmed, two ends of the locking bar member 1 were respectively provided with a fixing member 4, each of the fixing members 4 were joined with two sides of the treatment bed 2 to ensure that the locking bar member 1 were not prone to loose. At this time, the locking bar member 1 was below the isocenter 5.

In step S3, a calibration device 3 was provided, wherein the calibration device 3 was provided with at least one positioning point, so that the bottom part of the calibration device 3 was buckled with at least two positioning elements on the locking bar member 1. The calibration device 3 was a detector or a sensor. Generally speaking, the calibration device 3 was used by one skilled in the art to confirm the parameters of particle beams and the accuracy of the delivery of radiation dose. However, in the process of using the calibration device 3, the position of the calibration device 3 was adjusted manually and naked eyes were used to determine whether the mark on the calibration device 3 matched the laser beam in the treatment room to complete a positioning operation.

Through the method of the present invention, after the radiation position was successfully done for the first time, the position of the calibration device 3 was recorded, after the locking bar member 1 was fixed in a proper position in advance, the calibration device 3 was placed in the interior of a tank body having holes in its bottom part, or the calibration device 3 itself was provided with holes in its bottom part, the fixture 11 on the locking bar member 1 were buckled with the holes. Hereafter, the locking bar member 1 and the calibration device 3 are placed according to past records, any fine-adjustments or other tedious adjustment process was no longer required, reading errors caused by human naked eyes were avoided by the mechanical precision.

Finally, in step S4, the offset distance between the irradiation center of a radiation and the at least one positioning point of the calibration device 3 was calculated to obtain a value. If it was less than a specific value, it represented a positioning was completed. As mentioned earlier, the isocenter 5 of the radiation was the key to the success of a positioning.

Figure 3:
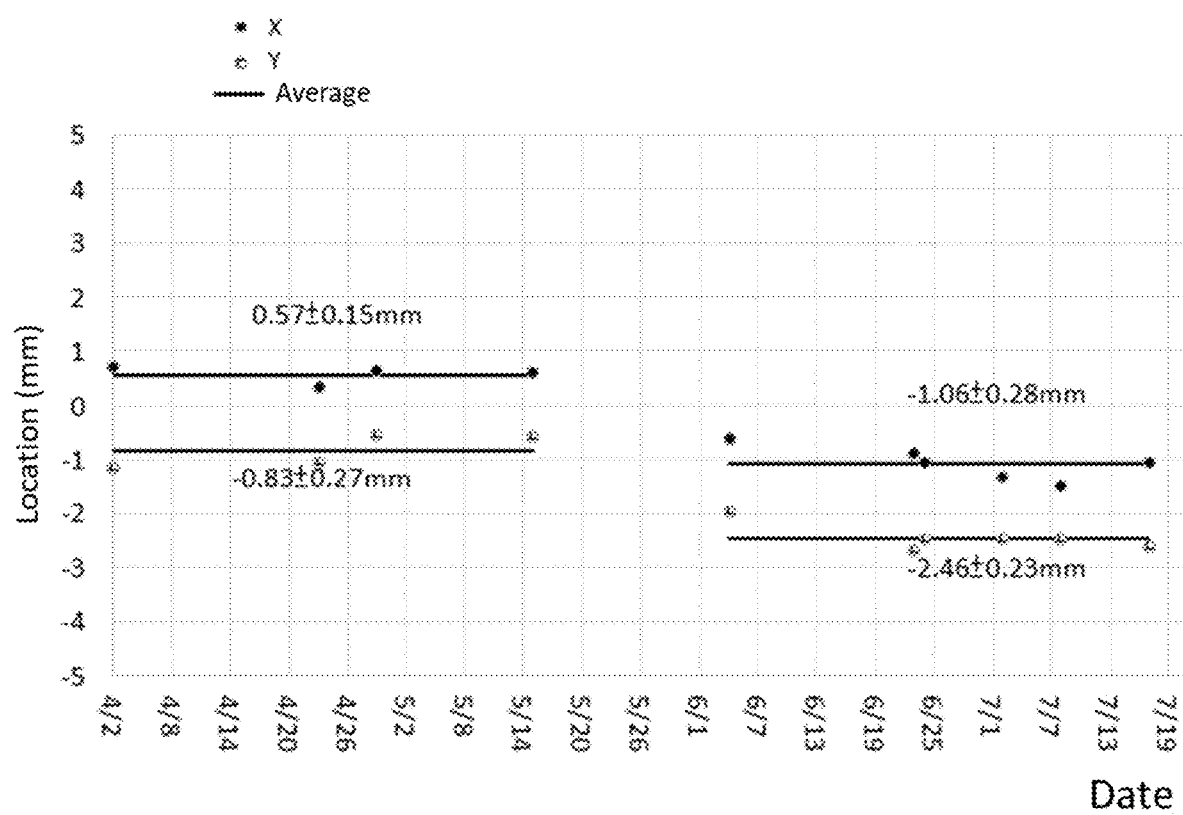
FIG. 3 is a function diagram of the present invention.

As shown in FIG. 3, according to the method proposed by the present invention, taking proton beam as an example, according to the data obtained from the center point of the calibration device 3, in this embodiment, before June, the center point of the calibration device 3 was measured four times. At that time, the reference coordinates corresponding to the center point of the calibration device 3 were (0.57 mm, −0.83 mm). There were deviations. It was still necessary to consider motion of the treatment bed 2 itself and whether it was necessary to correct. After all, as long as the relative position was close or the same every time when it was measured. Therefore, the deviation value generated by these four measurements was about 0.2 mm, proving that the positioning effect was actually achieved. After June, there were the annual maintenance and readjustments of the treatment bed 2, the reference coordinates corresponding to the center point of the calibration device 3 were (−1.06 mm, −2.46 mm), and the deviation value of each measurement was about 0.2 mm.

At the same time, the radiation position in the past daily quality assurance process required the detector and its connection to be arranged under a bright environment, subsequently the positioning process began after all lights were turned off. In a dark environment, deviations were generated from the path of the laser beam, the positioning line on the calibration device 3 and judgements made by human naked eyes when positioning was undertaken and repeat corrections were required. The process took longer than 2 minutes. Moreover, in the past, the requirement for radiation was not as strict as the requirements for proton beam position, and the deviation was usually close to about 1 mm. However, the requirement for proton beam position was higher than the requirements for photon rays. It only took 30 seconds for the present invention to complete this item of the quality assurance process, and the deviation value during the positioning could be as accurate as less than 0.5 mm, the deviation was even about 0.2 mm. The advantage of high-precision and short-time was the main feature of the present invention.

Figure 4:
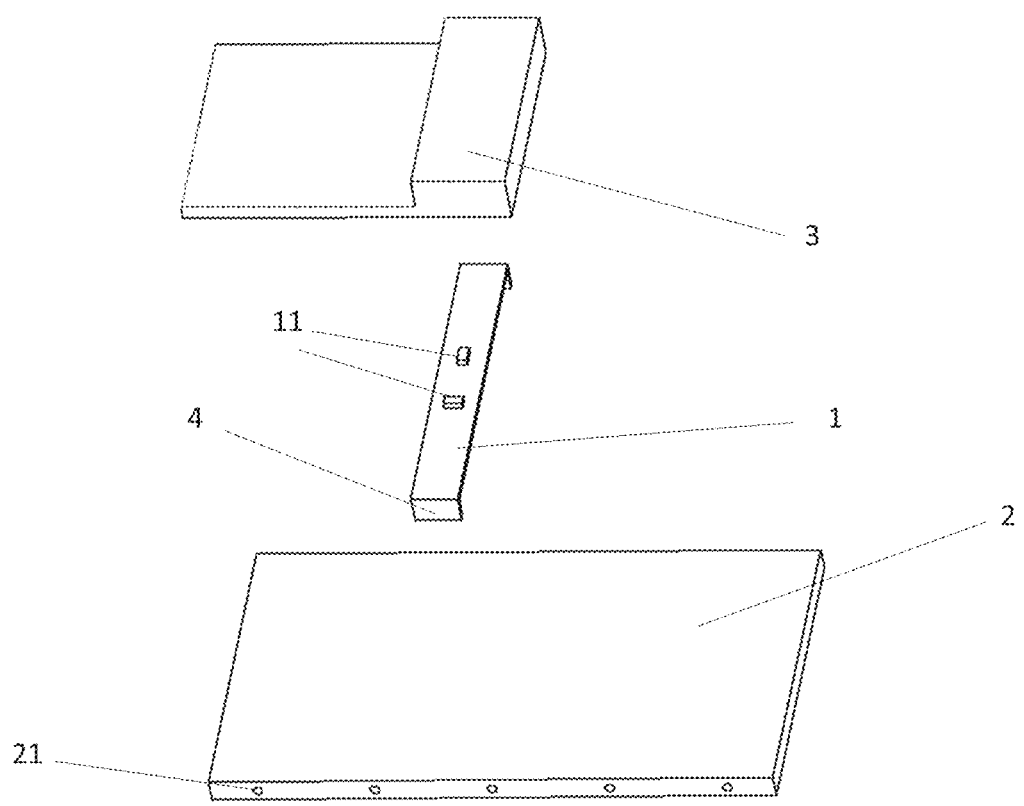
FIG. 4 is a three-dimensional view of one embodiment of the present invention.

FIG. 4 is one embodiment of the actual operation of the present invention. Taking the treatment bed 2 commonly used in hospitals as an example, two sides of the treatment bed 2 are usually provided with a plurality of holes 21. When radiation position was performed by the present invention, two ends of the locking bar members 1 were respectively provided with fixing members 4, wherein each of the fixing members 4 was provided with a convex part that could be buckled with the holes 21 of the treatment bed 2, and the locking bar member 1 was provided with two positioning elements, and the positioning elements could be buckled with the holes in the bottom part of the calibration device 3 as the positioning of irradiation location.

What is claimed is:

1. A method of radiation position, which includes:
   placing a locking bar member on a proper position of a treatment bed;
   selecting a position on one side of the treatment bed to be joined with one end of the locking bar member;
   providing a calibration device, wherein the calibration device is provided with at least one positioning point, so that the bottom part of the calibration device is buckled with at least two positioning elements on the locking bar member;
   and
   calculating an offset distance between an irradiation point of a radiation and the at least one positioning point of the calibration device to obtain a value, wherein if the value is less than a deviation value, it represents completion of a positioning.

2. A method of claim 1, wherein any one end of the locking bar member is provided with a fixing member, the fixing member is joined with one side of the treatment bed to ensure the locking bar member is not prone to loose.

3. A method of claim 1, wherein two ends of the locking bar members are respectively provided with fixing members, each of the fixing members are joined with two sides of the treatment bed to ensure the locking bar member is not prone to loose.

4. The method of claim 1, wherein the fixing members and the treatment bed are joined in a manner of screw fastening, buckling, or clamping.

5. The method of claim 1, wherein the bottom part of the calibration device is provided with at least two holes, and these holes are buckled with the positioning elements.

6. The method of claim 1, wherein the positioning elements are round, square, triangular or in any other shapes.

7. The method of claim 1, wherein the positioning elements are designed to be in different shapes as required to prevent the direction of the calibration device from being in opposite condition.

8. The method of claim 1, which further comprises the following step: preparing a tank body and placing the calibration device in the interior of the tank body.

9. The method of claim 8, wherein the bottom part of the tank body is provided with at least two holes, these holes are joined with the positioning elements of the locking bar member.

10. The method of claim 1, wherein the deviation value is less than 0.5 mm.

\* \* \* \* \*